United States Patent [19]

Kollmeyer

[11] Patent Number: 4,594,094

[45] Date of Patent: Jun. 10, 1986

[54] OXACYCLOALKANE-ALPHA-(THIO)CARBOXYLIC ACID DERIVATIVES AND USE AS PLANT GROWTH REGULATORS AND HERBICIDES

[75] Inventor: Willy D. Kollmeyer, Modesto, Calif.

[73] Assignee: Shell Oil Company, Houston, Tex.

[21] Appl. No.: 482,371

[22] Filed: Apr. 4, 1983

[51] Int. Cl.$^4$ ............... A01N 43/08; C07D 307/04; C07D 405/12

[52] U.S. Cl. ............................................. 71/88; 71/90; 71/92; 71/94; 71/95; 546/146; 546/147; 546/174; 546/175; 546/268; 546/283; 548/127; 548/128; 548/134; 548/136; 548/203; 548/204; 548/205; 548/214; 548/235; 548/247; 548/255; 548/262; 548/336; 548/374; 548/517; 549/60; 549/414; 549/425; 549/473; 549/484

[58] Field of Search ............... 549/414, 425, 473, 484; 546/268, 283; 71/88, 94

[56] References Cited

U.S. PATENT DOCUMENTS

| Re. 30,574 | 4/1981 | Barker et al. | 71/88 |
| 4,116,669 | 9/1978 | Barker et al. | 71/88 |
| 4,400,198 | 8/1983 | Orr et al. | 71/88 |
| 4,410,354 | 10/1983 | Sundelin et al. | 71/94 |

FOREIGN PATENT DOCUMENTS

| 00002 | 12/1978 | European Pat. Off. |
| 64306 | 11/1982 | European Pat. Off. |
| 2937645 | 4/1981 | Fed. Rep. of Germany |
| 2069488 | 8/1981 | United Kingdom |

Primary Examiner—Richard L. Raymond

[57] ABSTRACT

Oxacycloalkane-alpha-(thio)carboxylic acid derivatives of the formula

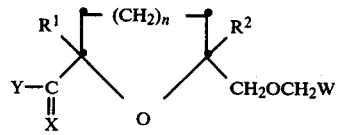

wherein $R^1$ and $R^2$ are H or optionally-substituted alkyl; n is 0 or 1; X is O or S and Y is $NR^4R^5$ or when X is O then Y is also OH or $OR^3$ in which $R^3$, $R^4$ and $R^5$ is H or an optionally-substituted hydrocarbyl group; and W is an optionally-substituted unsaturated, cycloalkyl, secondary alkyl, aromatic or heterocyclic group, are useful as plant growth regulators, herbicides, intermediates and the like.

10 Claims, No Drawings

OXACYCLOALKANE-ALPHA-(THIO)CARBOXYLIC ACID DERIVATIVES AND USE AS PLANT GROWTH REGULATORS AND HERBICIDES

BACKGROUND OF THE INVENTION

1. Field of the Invention

The present invention relates to novel oxacycloalkane-alpha-(thio)carboxylic acid derivatives, their use as intermediates to or as plant growth regulators and herbicides and to compositions containing the active derivatives.

2. Description of the Prior Art

U.S. Pat. Nos. 4,116,669, 4,289,884 and European Pat. No. 00,002 disclose certain tetrahydrofuran derivatives useful as herbicides. German Pat. No. 2,937,645 discloses certain tetrahydropyran derivatives useful as herbicides.

Applicant has discovered a new class of herbicides and plant growth regulators in which all the compounds are characterized by a (thio)carboxy group, usually most active as the (thio)amide derivatives.

SUMMARY OF THE INVENTION

The present invention is directed to an oxacycloalkane-alpha-(thio)carboxylic acid derivative compound of formula I

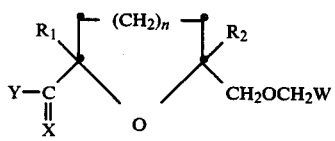

wherein $R^1$ and $R^2$ each independently is a hydrogen atom or an optionally substituted alkyl group containing from 1 to 6 carbon atoms; n is 0 or 1; X is O or S and Y is $NR^4R^5$ or when X is O then Y is also OH or $OR^3$ in which $R^3$, $R^4$ and $R^5$ is each independently a hydrogen atom or an optionally-substituted alkyl, alkenyl, alkynyl, cycloalkyl, aryl or aralkyl group containing up to 20 carbon atoms, preferably up to 10 carbon atoms; and W is an optionally substituted unsaturated group containing up to 4 carbon atoms, a cycloalkyl group containing 3 to 10 carbon atoms, a secondary alkyl group containing 3 to 10 carbon atoms, an aromatic group containing up to 14 carbon atoms or a heterocyclic group containing up to 14 carbon atoms. The compounds are useful as herbicides, plant growth regulators or intermediates and the like, as will be further discussed below.

Optionally substituents in the derivatives of formula I above include halogen atoms of atomic number 9 to 35, inclusive, or alkyl of 1 to 4 carbons, alkoxy of 1 to 4 carbon atoms or alkythio of 1 to 4 carbon atoms each optionally substituted by one or more halogen atoms, or equivalent kinds of substituents.

Non-limiting embodiments of the invention include those shown below

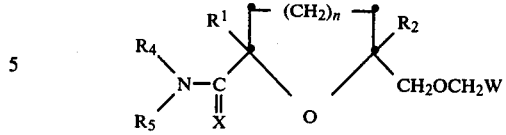

| n | $R^1$ | $R^2$ | W | X | $R^4$ | $R^5$ |
|---|-----|-----|---|---|-----|-----|
| 1 | Me | Et | 2-fluorophenyl | O | H | H |
| 1 | Me | Et | 2-fluorophenyl | S | H | H |
| 0 | Me | Et | 2,6-dichlorophenyl | O | H | H |
| 0 | Me | Et | 2,6-dichlorophenyl | S | H | H |
| 0 | Me | Et | 2-chloro-6-fluorophenyl | O | H | H |
| 0 | Me | Et | 2-chloro-6-fluorophenyl | S | H | H |
| 0 | Me | Et | 2,6-difluorophenyl | O | H | H |
| 0 | Me | Et | 2,6-difluorophenyl | S | H | H |
| 0 | Me | Et | 2-(trifluoromethyl)phenyl | O | H | H |
| 0 | Me | Et | 2-(trifluoromethyl)phenyl | S | H | H |
| 0 | Me | Et | 2-methoxyphenyl | O | H | H |
| 0 | Me | Et | 2-methoxyphenyl | S | H | H |
| 0 | Me | Et | 2-(methylthio)phenyl | O | H | H |
| 0 | Me | Et | 2-(methylthio)phenyl | S | H | H |
| 0 | Me | Et | 2-fluorophenyl | O | H | Me |
| 0 | Me | Et | 2-fluorophenyl | O | Me | Me |
| 0 | Me | Et | 2-fluorophenyl | O | H | allyl |
| 0 | Me | Et | 2-fluorophenyl | O | H | propargyl |
| 0 | Me | Et | 2-fluorophenyl | O | H | benzyl |
| 0 | Me | Et | 2-fluorophenyl | O | allyl | allyl |
| 0 | Me | Et | 2-fluorophenyl | O | H | phenyl | preferably in the cis isomer form, or in the trans isomer form, or as cis-trans mixtures thereof, and the precursor free carboxylic acids and methyl esters in which X is O.

In the derivatives of formula I, W is preferably an ethynyl group; a 2-pyridinyl group or a phenyl group optionally substituted by 1 or 2 chlorine or fluorine atoms or methyl groups. Three preferred subclasses of the invention are where R is 2-chlorophenyl, 2-methylphenyl and 2-fluorophenyl.

In the derivatives of formula I, $R^1$ and $R^2$ preferably each independently contain 1 or 2 carbon atoms, i.e. methyl or ethyl. $R^1$ is preferably a methyl group. $R^2$ is preferably an ethyl group.

In the derivatives of formula I, in the group Y, the $R^3$, $R^4$ and $R^5$ each independently is preferably a hydrogen atom, an alkyl group containing 1 to 6 carbon atoms, an alkenyl group containing up to 4 carbon atoms, an alkynyl group containing up to 4 carbon atoms, a phenyl group, or a benzyl group. Preferably, Y is $NR^4R^5$. X is preferably O (oxygen).

In the derivatives of formula I, n is preferably 0 (zero).

Compounds that possess substantially the same function as intermediates or have the same plant growth regulator or herbicidal utility as those described herein and which can be prepared in like manner are equivalents thereof and include compounds wherein, for example, W is an unsaturated, aromatic or (hetero)aromatic moiety, or cyclopropyl or 1-methylcyclopropyl, including but not limited to cyano, naphthyl, imidazolyl, triazolyl, thiadiazolyl, 2-quinolinyl, 1-isoquinolinyl, pyrrolyl, cyclohexenyl, N-methylimidazolyl, N-methylpyrazolyl, isoxazolyl, oxazolyl, isothiazolyl, thiazolyl, thienyl, 5-methyl-2-furanyl, and the like.

The compounds according to the invention can exist in several geometric forms, such as cis-configuration, trans-configuration or E and Z configuration as well as in optically-active forms. These individual forms as well as mixtures thereof are within the scope of the present invention. The various isomers of the derivatives of the invention may have different herbicidal or plant growth regulator properties. Thus, one may prefer deliberately to create mixtures or to resolve an isomer mixture to recover a more active isomer form or to prepare the more active form directly for use in the invention.

In general, the compounds of the invention wherein Y is $NR^4R^5$ have the highest herbicidal and plant growth regulator properties. The other compounds of the invention usually have some activity but are principal intermediates to those compounds where Y is $NR^4R^5$. The compounds of the invention also have utility as solvents or dispersing agents for pigments, paints, polymers and synthetic fibers.

(a) The materials of formula I wherein X is O and Y is —OH are prepared by treating the corresponding nitrile precursor with an alkali or alkali metal hydroxide, e.g., NaOH, KOH or the like, followed by a strong acid, e.g., HCl, $H_2SO_4$ or the like.

(b) The materials of formula I wherein X is O and Y is $OR^3$ are prepared by treating the corresponding carboxylic acid of (a) with an esterifying agent in a conventional manner. For example, by a method wherein diazomethane is generated in situ to obtain the methyl ester.

(c) The materials of formula I wherein X is O and Y is $NR^4R^5$ are prepared by treating the corresponding carboxylic acid ester of (b) with the appropriate amine, $NHR^4R^5$; or when n is 0, treating the nitrile precursor with water by use of hydrogen peroxide e.g., in the presence of a base, such as sodium hydroxide.

(d) The materials of formula I wherein X is S and Y is $NR^4R^5$ are prepared by treating the corresponding nitrile precursor with hydrogen sulfide, e.g. in the presence of a catalyst, such as triethanolamine.

The products of formula I(a), (b), (c) and (d) are recovered and purified by conventional techniques e.g., extraction, distillation and the like.

The nitrile precursors of the compounds of formula I wherein n is 1 are prepared, for example, by a Diels-Alder type reaction of an alkyl vinyl ketone with methyl methacrylate or methyl ethacrylate, transesterification of the resulting methyl ester adducts to the n-butyl ester, separation of the ester from the alkyl vinyl ketone dimer, reduction of the separated ester, e.g., with LiAlH$_4$, to the corresponding methanol derivative, etherification with WCH$_2$Cl in the presence of NaH, and treatment with HCN to introduce the alpha-cyano substituent. In a specific example, wherein $R^1$ and $R^2$ are both $CH_3$, the starting materials are methyl vinyl ketone and methyl methacrylate.

The nitrile precursors of the compounds of formula I wherein n is 0 are prepared by epoxidation-cyclization of novel cyanohydrins, i.e., 2-hydroxy-5-hexenenitrile or 2,5-dialkyl-2-hydroxy-5-hexenenitrile, of the formula

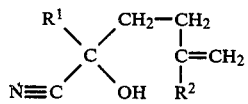

wherein $R^1$ and $R^2$ are as defined for formula I, e.g., by epoxidation with m-chloroperbenzoic acid, treatment of the resulting epoxy cyanohydrin with hydrochloric acid to yield the novel 2-cyano-tetrahydrofuran-5-methanol of the formula

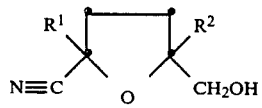

wherein $R^1$ and $R^2$ are as defined for formula I, and subsequent etherification e.g., with WCH$_2$Cl. The 2-hydroxy-5-hexenenitriles are prepared by treating the corresponding unsaturated ketone with, acetic anhydride and potassium cyanide by the general procedure of R. Franks, R. Berry, and O. Shotwell, *J. Am. Chem. Soc.*, 71, 3889 (1949). The unsaturated ketones are prepared by (1) reaction of an aldehyde with an unsaturated Grignard reagent followed by selective oxidation of the hydroxy group to a ketone, or (2) reaction of an allyl chloride with an alkanedione as described, for example, in F. Barbot, D. Mesnard, and L. Miginiac, *Organic Preparations and Procedures International* 10, 261 (1978).

The etherification which introduces the group W is conducted by treating the appropriate dihydropyranmethanol derivative or 5-cyanotetrahydrofuranmethanol derivative with a compound of the formula WCH$_2$X in which W is defined as in formula I above and X is a halogen atom, such as bromine, chlorine or iodine, or is a mesyloxy, tosyloxy group or the like, in the presence of a base and an inert diluent. The base is suitably an alkali metal hydride, hydroxide or carbonate, including, for example, sodium hydride, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. The reaction can be conducted in a two-phase system, preferably in the presence of a phase-transfer catalyst. For example, the system is aqueous sodium or potassium hydroxide solution with toluene or methylene chloride and the phase-transfer catalyst is an ammonium compound such as tetra-n-butyl-ammonium chloride, bromide, or hydrogen sulfate, triethyl-benzylammonium chloride or the like. The reaction is usually carried out under normal pressures and ambient temperatures. Suitable temperatures for the reaction are from about 0° to about 120° C., preferably from about 20° to about 100° C. The product ethers are recovered and isolated by conventional techniques.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

3,4-Dihydro-2,6-dimethyl-2H-pyran-2-carboxylic Acid, Butyl Ester

Equimolar amounts of methyl methacrylate (20.0 g) and methyl vinyl ketone (14.0 g) were sealed in a 150 ml stainless steel bomb and kept at 200° C. for two hours. This batch process was repeated several times (1.1 moles total for each reagent). The combined reaction mixture was then distilled to give 55.0 g liquid with bp 42°–52° C. (0.02 torr). By glc the product was a ca 2:1 mixture of the Diels-Alder dimer of methyl vinyl ketone and the methyl ester of the desired adduct. 20.0 g of this mixture was added to 200 ml 1-butanol containing 0.5 g of 50% sodium hydride-mineral oil dispersion. After 35 minutes at ca 25° C., the solvent was stripped, the residue was taken up in pentane, and the organic phase was washed with aqueous sodium bicarbonate and dried over potassium carbonate. After a forerun of the methyl vinyl ketone dimer, careful fractional distillation gave 4.15 g colorless product with bp 62° C. (0.02 torr).

EMBODIMENT 2

3,4-Dihydro-2,6-dimethyl-2H-pyran-2-methanol

A mixture of 3,4-dihydro-2,6-dimethyl-2H-pyran-2-carboxylic acid butyl ester (23.7 g) and lithium aluminum hydride (4.2 g) in 160 ml tetrahydrofuran was heated briefly to reflux and then allowed to cool. After 3.5 hours, excess hydride was destroyed by addition of ethyl acetate (70 ml). Volatile solvents were then stripped, and the residue was treated with 100 ml 15% aqueous sodium hydroxide and extracted with ether. The organic phase was dried over potassium carbonate and distilled to afford 12.3 g colorless product with bp 48°–49° C. (0.03 torr).

EMBODIMENT 3

3,4-Dihydro-2,6-dimethyl-2-[(phenylmethoxy)methyl]-2H-pyran

A mixture of 3,4-dihydro-2,6-dimethyl-2H-pyran-2-methanol (5.8 g) and benzyl chloride (5.2 g) in 50% aqueous sodium hydroxide (16 g) and 10 ml methylene chloride was treated with 0.7 g tetrabutylammonium hydrogen sulfate. After stirring vigorously for 21 hours at room temperature, the mixture was diluted with more methylene chloride and water to facilitate phase separation. The organic phase was separated, washed with water, dried over potassium carbonate and concentrated. Distillation gave 7.6 g colorless liquid with bp 101°–102° C. (0.02 torr).

EMBODIMENT 4

Tetrahydro-2,6-dimethyl-6-[(phenylmethoxy)methyl]-2H-pyran-2-carbonitrile, Mixture of cis (Z) and trans (E) Isomers A mixture of 15.0 g 3,4-dihydro-2,6-dimethyl-2-[(phenylmethoxy)methyl]-2H-pyran, 1.75 g liquid hydrogen cyanide, and 0.1 g pyridine sealed in a 30 ml glass bomb was kept at 150° C. for 16 hours. The resulting dark brown solution was distilled (Kugelrohr) to give 15.7 g colorless product, bp 112°–118° C. (0.01 torr), as an isomeric mixture, ca 4:6, cis:trans, based on NMR spectrum in CDCl$_3$.

EMBODIMENT 5

Tetrahydro-2,6-dimethyl-6-[(phenylmethoxy)methyl]-2H-pyran-2-carbonitrile, Cis (Z) Isomer The product of Embodiment 4 was separated into its cis and trans isomeric components on a Waters 500 Preparative HPLC using a silica gel column, 9:1 pentane:ether as eluent, and one recycle. A total of 14.9 g of the product of Embodiment 4 was processed in ca 3 g batches. The purified isomers were isolated as oils, bp not determined; 4.5 g cis (Z) isomer was obtained.

EMBODIMENT 6

Tetrahydro-2,6-dimethyl-6-[(phenylmethoxy)methyl)]-2H-pyran-2-carbonitrile, Trans (E) Isomer The trans (E) isomer from the above separation in Embodiment 5 was secured in the amount of 8.1 g.

EMBODIMENT 7

Tetrahydro-2,6-dimethyl-6-[(phenylmethoxy)methyl]-2H-pyran-2-carboxylic Acid, cis-Isomer A mixture of 1.50 g of the cis-nitrile of Embodiment 5 and 3.30 g potassium hydroxide in 30 ml water and 15 ml ethanol was heated at reflux for 19 hours. Upon cooling, the mixture was diluted with water and extracted with pentane. The cooled aqueous phase was then acidified with dilute hydrochloric acid and extracted with diethyl ether. The dried (MgSO$_4$) extract was concentrated to give 1.50 g of the desired product as a viscous oil; bp not determined.

EMBODIMENT 8

Tetrahydro-2,6-dimethyl-6-[(phenylmethoxy)methyl]-2H-pyran-2-carboxylic Acid, Methyl Ester, cis-Isomer Ethereal diazomethane generated from p-toluenesulfonylmethylnitrosoamide (Diazald ® Kit from Aldrich Chemical Co.) was distilled into a receiver containing 3.05 g of cis-acid of Embodiment 7 in 10 ml diethyl ether until the characteristic yellow color of diazomethane persisted. The reaction mixture was then titrated to a colorless state by addition of acetic acid. Removal of solvent at reduced pressure gave a quantitative yield of the desired product as an oil; bp not determined.

EMBODIMENT 9

Tetrahydro-2,6-dimethyl-6-[(phenylmethoxy)methyl]-2H-pyran-2-carboxylic Acid, Methyl Ester, Trans-Isomer By the above procedures of Embodiments 6, 7 and 8, the trans-acid was prepared and converted into the desired product, which was a light amber oil, bp not determined.

EMBODIMENT 10

Tetrahydro-2,6-dimethyl-N-phenyl-6-[(phenylmethoxy)]-2H-pyran-2-carboxamide

A mixture of 1.25 g of the trans-methyl ester of Embodiment 9 above, 3.8 g freshly distilled aniline, and a catalytic amount of sodium hydride (ca 100 mg) was sealed in a glass bomb and kept at 220° C. The reaction was periodically monitored by tlc and glc. This indicated that as the starting material disappeared, two new components were forming. After 72 hours, the mixture was cooled and diluted with ether. The organic phase was washed successively with water, dilute hydrochloric acid, and water. After drying (MgSO$_4$) and removal of solvent, the residue was distilled in a Kugelrohr apparatus at reduced pressure (0.01 torr) yielding three fractions: bp 25°–120° C., bp 120°–155° C., and bp 173°–180° C. The highest boiling fraction, 1.0 g, consisted of the two new components which had been observed during the course of the reaction by tlc and glc.

Isomer A Separation of the highest boiling fraction was achieved on a Waters Model 500 Preparative HPLC using a silica gel column and 75:25 pentane ether as eluent. The more mobile component (isomer A), which was first isolated as 0.35 g oil, crystallized from pentane to afford 0.20 g white solid with mp 75°–75.5° C.

Isomer B The slower moving component of the highest boiling fraction was secured as 0.50 g of oil which was also crystallized from pentane to yield 0.20 g white solid with mp 55°–56° C.

EMBODIMENT 11

Tetrahydro-2,6-dimethyl-6-[(phenylmethoxy)methyl]-N-(2-propenyl)-2H-pyran-2-carboxamide, cis-Isomer A mixture of 0.50 g of the cis-ester of Embodiment 8 and a large excess (16 ml) of allylamine was placed in s stainless steel bomb and kept at 200° C. for 22 hours. The mixture was then diluted with methylene chloride and washed with aqueous sodium bicarbonate. After drying over magnesium sulfate and removal of solvent and excess amine, the residue was distilled to give an amber oil, bp 80°–150° C. (0.01 torr, Kugelrohr apparatus). Further purification by column chromatography on silica gel (Davison Chemical, grade 950) using an elution gradient starting with methylene chloride and finishing with ether afforded 0.40 g of the desired product as a viscous liquid.

EMBODIMENT 12

Tetrahydro-2,6-dimethyl-6-[(phenylmethoxy)methyl]-N-(2-propenyl)-2H-pyran-2-carboxamide, Trans-Isomer A mixture of 0.75 g (2.7 mmol) of the trans-ester of Embodiment 9 and excess (20 ml) allylamine was heated at 200° C. for 76 hours. After workup as above, but without Kugelrohr distillation, the crude oil was column chromatographed on silica gel (Davison Chemical, grade 950) using a gradient elution starting with methylene chloride and finishing with ether. This provided 0.15 g of the desired product as an amber oil.

EMBODIMENT 13

1-Chloro-2,2-bis(chloromethyl)butane

To a mixture of 134 g 2,2-bis(hydroxymethyl)butanol, 79.1 g pyridine and 100 ml cyclohexane was added 535 g thionyl chloride with provision for scrubbing evolved acid gases. The mixture was heated at reflux for six hours and then allowed to stand at room temperature over a weekend. After removing volatiles (rotary evaporator), the residue was taken up in methylene chloride and washed once with water and then twice with concentrated sulfuric acid. The solution was dried (magnesium sulfate) and distilled to give 148 g of product with bp 64°–65° C. (0.04 torr).

EMBODIMENT 14

5-Methylene-2-heptanol

A solution of 3-methylenepentyl magnesium chloride was prepared from 56.86 g 1-chloro-2,2-bis(chloromethyl)butane and 14.59 g magnesium with exclusion of moisture ($N_2$) by adding the halide in 60 ml tetrahydrofuran to the metal in 90 ml of the same solvent at such a rate that reflux was maintained. A small amount of iodine and methyl iodide was used to initiate the reaction. The mixture was refluxed for an additional one hour. Then with cooling (dry ice-acetone bath), 44.05 g acetaldehyde in 60 ml tetrahydrofuran was added dropwise at −30° C. After warming to −10° C., the reaction mixture was quenched first with 360 ml water and then 180 ml 15% sulfuric acid, and extracted with methylene chloride. The extract was washed with water and 10% sodium bicarbonate, dried over magnesium sulfate, and distilled. The product weighed 26.80 g, bp 90°–93° C. (30 torr).

EMBODIMENT 15

5-Methylene-2-heptanone

With exclusion of moisture ($N_2$) and cooling (−19° C., carbon tetrachloride-dry ice slush bath), a solution of 19.23 g 5-methylene-2-heptanol in toluene was added to a stirred mixture of 30.04 g N-chlorosuccinimide and 19.10 g dimethyl sulfide in toluene. The mixture was allowed to warm to ca 25° C. over a two-hour period. Then 23.2 g triethylamine was added. After five minutes, the reaction mixture was diluted two-fold with ether. Upon washing with 1% hydrochloric acid and then water, the organic phase was dried (magnesium sulfate) and concentrated. Distillation afforded 6.85 g product with bp 73°–76° C. (20 torr).

EMBODIMENT 16

5-Ethyl-2-hydroxy-2-methyl-5-hexenenitrile

To a cooled (ice-bath) solution of 20 g 5-methylene-2-heptanone in 33.5 g acetic anhydride was added dropwise a solution of 21.3 g potassium cyanide in 40 ml water. After stirring overnight at ca 25° C., the mixture was diluted with excess saturated aqueous sodium carbonate. After extraction with methylene chloride, the organic phase was dried over magnesium sulfate. Removal of solvent (rotary evaporator) gave 20.1 g crude cyanohydrin that was immediately used in the following epoxidation-cyclization step of Embodiment 17.

EMBODIMENT 17

5-Cyano-2-ethyl-5-methyltetrahydro-2-furanmethanol

To a cooled (ice-bath) and stirred mixture of 24.87 g m-chloroperbenzoic acid in 360 ml methylene chloride was added dropwise 20.1 g of the cyanohydrin of Embodiment 16. After addition was completed, the mixture was allowed to warm to room temperature (ca 25° C.) and stand over a weekend with exclusion of moisture ($N_2$). Cyclization of the intermediate epoxy cyanohydrin was then effected by treatment with 150 ml 0.12N hydrochloric acid. The resulting heterogeneous system was stirred vigorously for 2 hours and then filtered. The organic phase was separated and washed with 10% aqueous sodium bicarbonate. After drying over magnesium sulfate, 12.94 g of liquid product was obtained by Kugelrohr distillation, bp 85°–100° C. (0.3 torr).

EMBODIMENT 18–26

Cyano Ether Derivatives

One molecular equivalent of 5-cyano-2-ethyl-5-methyltetrahydro-2-furanmethanol was converted into the sodium alkoxide derivative by treatment with 1.1 molecular equivalents of sodium hydride in dry dimethylformamide with ice-bath cooling. When hydrogen evolution ceased, 1.1 equivalents of the appropriate benzylic chloride was added. In the case of 2-picolinyl chloride, this substance was freshly liberated from its hydrochloride salt by aqueous neutralization with potassium carbonate and extraction with methylene chloride; rapid removal of this solvent at reduced pressure gave the crude 2-picolinyl chloride which was used immediately. After addition of the appropriate benzylic or 2-picolinyl chloride, the reaction mixture was stirred for 1½ hours at ca 25° C. Then the mixture was diluted with 10 volumes of water and extracted with either pentane or ether. The dried (MgSO₄) extract, upon removal of solvent, gave a crude product consisting of geometric isomers of the desired substance and small amounts of the symmetrical dibenzyl ether as a minor byproduct. Purification by preparative hplc (Waters 500 Instrument, silica gel column) using hexane containing 5-15 volume percent ether as eluent gave varying degrees of isomer separation. In the case of the 2-picolinyl product, hexane with 40 volume percent ethyl acetate was employed.

TABLE 1

5-CYANO ETHER DERIVATIVES

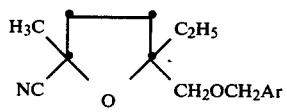

| Embodiment | Ar | Isomer Content$^{(a)}$ (cis:trans) Z:E |
|---|---|---|
| 18 | 2-chlorophenyl | 10:1 |
| 19 | 2-chlorophenyl | 1:1 |
| 20 | 2-methylphenyl | 3:1 |
| 21 | 2-methylphenyl | 1:3 |
| 22 | 2-pyridinyl | not determined |
| 23 | 2-pyridinyl | >10:1 |
| 24 | 2-pyridinyl | >1:10 |
| 25 | 2-fluorophenyl | 1:1 |
| 26 | 2-fluorophenyl | 1:2 |

$^{(a)}$Estimated by nmr integrations of the —CH₂OCH₂— signals.

EMBODIMENT 27

Tetrahydro-5-ethyl-2-methyl-5-[(2-chlorophenylmethoxy)methyl]-2-furanthiocarboxamide (Trans-Isomer)

Excess hydrogen sulfide was condensed into a stainless steel bomb containing 2.94 g of the chromatographically purified trans-nitrile, tetrahydro-2-methyl-5-ethyl-5-[(2-chlorophenylmethoxy)methyl]-2-furancarbonitrile, (ca>9:1 trans-cis by proton NMR), 10 ml ethanol, and 0.15 g triethanolamine catalyst. The sealed bomb was kept at 55±3° C. for 6 hours during which time the internal pressure rose to 350 psi. After cooling, the reaction mixture was concentrated on a rotary evaporator. The residue was purified by dry column chromatography on silica gel using 96.4 hexane:tetrahydrofuran as eluent. The white cyrstalline desired product weighed 1.10 g, mp 78°-80° C.

EMBODIMENT 28

Tetrahydro-5-ethyl-2-methyl-5-[(2-chlorophenylmethoxy)methyl]-2-furanthiocarboxamide (Cis-Isomer)

As described in Embodiment 27 above, 3.05 g of chromatographically purified cis-nitrile, tetrahydro-2-methyl-5-ethyl-5-[(2-chlorophenylmethoxy)methyl]-2-furancarbonitrile, (ca 8:2 cis:trans by proton NMR) was treated with excess hydrogen sulfide and chromatographed. Owing to the trans-nitrile contaminant in the starting material, the first isolated was the more mobile trans-thioamide of Embodiment 27. Later fractions afforded the predominant and less-mobile desired cis-thioamide, mp 67°-78° C. By gc/ms (electron impact) the product consisted of a major component whose fragmentation pattern was consistent with the desired thioamide, while the minor component was identified as the precursor nitrile by the fragmentation pattern which did not show a parent ion.

EMBODIMENT 29

Tetrahydro-5-ethyl-2-methyl-5-[(2-fluorophenyl)methoxy]-2-furanthiocarboxamides

Excess hydrogen sulfide was condensed into a stainless steel bomb containing 9.10 g of a distilled isomeric mixture (ca 61:49 trans:cis) of the corresponding nitriles of Embodiment 25 and 26, 0.49 g triethanolamine, and 35 ml ethanol. The sealed bomb was kept at 70° C. until tlc indicated disappearance of starting nitriles. Upon cooling, solvent was removed at reduced pressure. The residue was freed of highly polar impurities by chromatography on a short, dry, silica gel column using ethyl acetate as eluent. The resulting crude product was then further separated by preparative hplc on a Waters 500 instrument with silica gel column using a gradient ranging from 10-20 volume percent ethyl acetate in hexane. Fractions were assayed by tlc, pooled as appropriate, and concentrated. The first material to elute was 4.81 g recovered nitriles. The next major component was Isomer A followed by Isomer B.

Isomer A The more mobile of the two isomers was an oil, bp not determined, that weighed 1.60 g; gc/ms indicated two major components (17:75) which corresponded to the starting nitrile, and the desired thioamide.

Isomer B The less mobile of the two isomers was a white solid, 1.32 g, with mp 90°-93° C.; gc/ms (electron impact) indicated two components (23:77) which corresponded to the starting nitrile and the desired thioamide.

EMBODIMENT 30

Tetrahydro-5-ethyl-2-methyl-5-[(2-fluorophenylmethoxy)methyl]-2-furancarboxamide Isomers The precursor nitrile of Embodiment 25 was prepared in dimethylformamide solution containing sodium hydride as described previously. The nitrile, after purification by Kugelrohr distillation, bp 120°-125° C. (0.01 torr), 67% yield, was an isomeric mixture by ¹HNMR; gc/ms suggested a ratio of 61:49 cis-trans which was in qualitative agreement with the ¹HNMR spectrum.

After a brief exotherm to 45° C., a mixture of 2.77 g of the above nitrile, 4.0 ml 30% aqueous hydrogen peroxide, 0.4 ml 6N sodium hydroxide and 5 ml ethanol was kept at 60° C. until tlc indicated complete consumption of the nitrile (ca 2 hours). Then the warm mixture was neutralized with 0.13 g concentrated sulfuric acid in 3 ml water, cooled, diluted with 100 ml water, and extracted three times with 150 ml of diethyl ether each. The combined ether extract was washed with 5% aqueous sodium carbonate, dried (MgSO₄), and concentrated to give 1.62 g crude, oily product. By gc/ms the oil appeared to be a ca 2:1 mixture of the desired carboxamide isomers.

The alkaline hydrogen peroxide treatment was repeated with a further 5.87 g of the above nitrile to give an additional 5.89 g oil. The combined crude carboxamide product from both runs was then subjected to a preliminary clean up by dry column chromatography on silica gel with ethyl acetate eluent. Isomer separation was achieved by preparative hplc on silica gel elution with (1) 6 liters of a linear gradient of 20-40% diethyl ether in methylene chloride, (2) 4 liters 40% ether in methylene chloride, and (3) 1 liter of ether. Fractions of ca 200 ml were collected.

Isomer A. Cis-Isomer Concentration of fractions 24–30 gave 2.46 g of the desired oil.

Isomer B. Cis/Trans-Mixture Evaporation of fractions 31–34 provided 1.53 g of the desired oil.

Isomer C. Trans-Isomer Fractions 35–50 afforded 2.93 g of the desired oil.

EMBODIMENTS 31–35

Following procedures similar to those set forth in Embodiments 27, 28 and 29 above, additional alpha-(thio)carboxylic acid derivatives were prepared as set forth in Table 2 below.

TABLE 2
ALPHA-(THIO)CARBOXYLIC ACID DERIVATIVES

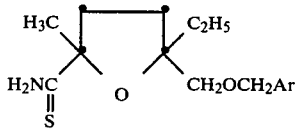

| Embodiment | W | Composition[a] Thioamide/Nitrile | MP (°C.) or Oil | TLC Isomer |
|---|---|---|---|---|
| 31 | phenyl | 86:14[c] | oil | fast |
| 32 | phenyl | 79:21[d] | 90–93 | slow |
| 33 | 2-methylphenyl | 93:7 | oil | fast |
| 34 | 2-methylphenyl | 89:11 | 90–93 | slow |
| 35 | 2-pyridinyl | 88:12[b] | 87–90 | both[b] |

[a]Ratio determined by gc/ms; however see footnotes (c) and (d).
[b]Thiocarboxamide isomers were not separable by preparative hplc or tlc; gc/ms indicated that product consisted of 12:56:32 starting nitrile:- more mobile thioamide:- less mobile thioamide.
[c]Reverse phase hplc indicated the presence of 2.8% nitrile.
[d]Reverse phase hplc could not detect any nitrile.

The invention includes a method of regulating plant growth, including combating unwanted plants, which comprises applying to the locus an effective amount of a compound of Formula I. For example, the compounds can change plant morphology, depress the growth of plants or kill plants. As herbicides, they appear to be more effective when applied preemergence or pre-plant incorporated, particularly to control grassy weeds. For application, the compound generally is applied most effectively by formulating it with a suitable inert carrier or surface active agent, or both. The invention therefore also includes compositions suitable for regulating plant growth, including combating unwanted plants, such compositions comprising an inert carrier or surface-active agent, or both, and as active ingredient at least one active compound of formula I, preferably wherein Y is NR$^4$R$^5$.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone, isophorone and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and-/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Growth regulator or protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in regulating plant growth, including combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*
Mustard—*Brassica kaber*
Grain sorghum—*Sorghum vulgare* (Pioneer 265)
Corn—*Zea maize* (deKalb X363)
Cotton—*Gossypium hirsutum* (Acala SJ-2)
Soybean—*Glycine max* (Amsoy 71)
Wheat—*Triticum aestivum* (Cajeme 71)
Sugar beet—*Beta vulgaris*
Cocklebur—*Xanthum pennsylvanicum*

Primary Tests—Preemergence Activity

The preemergence (soil) activity of compounds of the invention was evaluated by planting seeds of barnyardgrass, garden cress, downy brome, velvetleaf, yellow foxtail, and sicklepod in test tubes, nominally measuring 25×200 mm, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 mg of the test compound per each tube containing the seeds of the other plants. The dosages were approximately 22 and 2.2 lb of test compound per acre, respectively. The seeds were planted on top of the treated soil and covered with about 1.5 cubic centimeters of untreated soil. The planted tubes were held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

Primary Tests—Postemergence Activity

The postemergence (foliar) activity of compounds of the invention was evaluated by spraying 10-day-old large crabgrass plants, 13-day-old redroot pigweed plants, 6-day-old Johnsongrass plants, 9-day-old velvetleaf plants, 9-day-old yellow foxtail plants and 9-day-old sicklepod plants to runoff with a liquid formulation of the test compound. The crabgrass and pigweed plants were sprayed with 2.4 ml of a 0.25% solution (about 10 lb of the test compound per acre), and other plants were sprayed with 2.4 ml of a 0.025% solution (about 1 lb of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence activity tests conducted on the compounds of the invention are set forth in Table 1.

TABLE 1

| | HERBICIDAL ACTIVITY | | | | | | | | | | | |
| --- | --- | --- | --- | --- | --- | --- | --- | --- | --- | --- | --- | --- |
| | Preemergence (Soil) | | | | | | Postemergence (Foliar) | | | | | |
| Embodiment | Barnyard Grass | Garden Cress | Downy Brome | Velvet Leaf | Yellow Foxtail | Sicklepod | Crab Grass | Pig Weed | Johnson Grass | Velvet Leaf | Yellow Foxtail | Sicklepod |
| 30C | 9 | 8 | 7 | 6 | 8 | 7 | 4 | 6 | 2 | 5 | 1 | 3 |

TABLE 1-continued

| | HERBICIDAL ACTIVITY | | | | | | | | | | | |
|---|---|---|---|---|---|---|---|---|---|---|---|---|
| | Preemergence (Soil) | | | | | | Postemergence (Foliar) | | | | | |
| Embodiment | Barnyard Grass | Garden Cress | Downy Brome | Velvet Leaf | Yellow Foxtail | Sicklepod | Crab Grass | Pig Weed | Johnson Grass | Velvet Leaf | Yellow Foxtail | Sicklepod |
| 30B | 9 | 8 | 7 | 6 | 8 | 6 | 5 | 6 | 0 | 6 | 1 | 5 |
| 30A | 9 | 8 | 6 | 5 | 7 | 6 | 4 | 6 | 2 | 4 | 2 | 3 |
| 11 | 0 | 5 | 0 | 0 | 0 | 0 | 3 | 7 | 0 | 0 | 0 | 1 |
| 12 | 6 | 5 | 2 | 2 | 2 | 0 | 6 | 4 | 0 | 0 | 0 | 2 |
| 10B | 7 | 0 | 0 | 0 | 0 | 0 | 4 | 2 | 0 | 1 | 3 | 5 |
| 32 | 9 | 8 | 7 | 3 | 8 | 6 | 6 | 8 | 2 | 4 | 5 | 2 |
| 31 | 9 | 7 | 7 | 3 | 7 | 4 | 1 | 3 | 1 | 3 | 2 | 2 |
| 28 | 9 | 7 | 9 | 6 | 6 | 2 | 7 | 8 | 6 | 6 | 7 | 3 |
| 27 | 7 | 7 | 4 | 3 | 4 | 2 | 7 | 6 | 2 | 5 | 5 | 3 |
| 34 | 9 | 7 | 7 | 5 | 6 | 4 | 7 | 7 | 6 | 6 | — | 2 |
| 33 | 8 | 7 | 5 | 6 | 5 | 4 | 6 | 3 | 0 | 4 | — | 2 |
| 29B | 9 | 8 | 8 | 5 | 8 | 6 | 6 | 5 | 3 | 5 | 5 | 4 |
| 29A | 9 | 8 | 7 | 4 | 7 | 5 | 6 | 5 | 2 | 3 | 5 | 2 |
| 35 | 9 | 8 | 6 | 3 | 8 | 5 | 3 | 5 | 2 | 4 | 2 | 3 |
| 8 | 8 | 5 | 4 | 3 | 0 | 0 | 4 | 5 | 0 | 1 | 0 | 3 |
| 9B | 9 | 6 | 7 | 2 | 0 | 2 | 3 | 6 | 0 | 3 | 0 | 2 |
| 7 | 6 | 4 | 0 | 0 | 0 | 0 | 2 | 5 | 0 | 0 | 0 | 2 |
| 9A | 0 | 4 | 0 | 3 | 0 | 0 | 2 | 5 | 0 | 0 | 0 | 1 |

— means "no test"

What is claimed is:

1. A (thio)carboxylic acid derivative of the formula

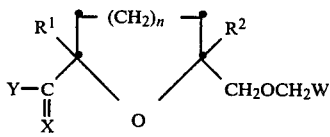

wherein $R^1$ and $R^2$ each independently is a hydrogen atom or an optionally-substituted alkyl group containing from 1 to 6 carbon atoms; n is 0 or 1; X is O or S and Y is $NR^4R^5$ or when X is O then Y is also OH or $OR^3$ in which $R^3$, $R^4$ and $R^5$ is independently a hydrogen atom or an optionally-substituted alkyl, alkenyl, alkynyl, cycloalkyl, aryl or aralkyl group containing up to 10 carbon atoms; and W is an optionally substituted unsaturated group containing up to 4 carbon atoms, a cycloalkyl group containing 3 to 10 carbon atoms, a secondary alkyl group containing 3 to 10 carbon atoms, an aromatic group containing up to 14 carbon atoms or a heterocyclic group containing up to 14 carbon atoms, in which the optional substituents for $R^1$, $R^2$, $R^3$, $R^4$, $R^5$ and W are halogen atoms of atomic number 9 to 35, inclusive, ior alkyl, alkoxy or alkylthio groups containing 1 to 4 carbon atoms, each optionally substituted by one or more halogen atoms.

2. A (thio)carboxylic acid derivative according to claim 1 wherein W is an ethynyl group, a 2-pyridinyl group or a phenyl group optionally substituted by 1 or 2 chlorine or fluorine atoms or methyl groups.

3. A (thio)carboxylic acid derivative according to claim 2 wherein Y is $NR^4R^5$.

4. A (thio)carboxylic acid derivative according to claim 3 wherein $R^1$ and $R^2$ each independently is a methyl or ethyl group.

5. A (thio)carboxylic acid derivative according to claim 4 wherein W is a 2-chlorophenyl, a 2-fluorophenyl or 2-methylphenyl group.

6. A (thio)carboxylic acid derivative according to claim 5 wherein n is 0.

7. A derivative according to claim 6 wherein X is O.

8. A plant growth regulating composition comprising an effective amount of an active ingredient of a compound according to claim 1 in which Y is $NR^4R^5$ or when X is O then Y is also $OR^3$ and at least one carrier or surface-active agent.

9. A method of regulating plant growth at a locus comprises applying to the locus or the plant an effective amount of an active ingredient of a compound according to claim 1 in which Y is $NR^4R^5$ or when X is O then Y is also $OR^3$.

10. A method according to claim 9 wherein plant growth is regulated by depressing growth of the plant or by killing the plant.

* * * * *